United States Patent [19]

Deenadayalu

[11] Patent Number: 4,572,180
[45] Date of Patent: Feb. 25, 1986

[54] LIGHTED EAR CANAL CURETTE INSTRUMENT

[76] Inventor: R. Paul Deenadayalu, 298 Shadywood Dr., Dayton, Ohio 45415

[21] Appl. No.: 552,968

[22] Filed: Nov. 17, 1983

[51] Int. Cl.[4] .............................................. A61B 17/22
[52] U.S. Cl. ...................................... 128/304; 128/23
[58] Field of Search ...................... 128/304, 23; 433/29

[56] References Cited

U.S. PATENT DOCUMENTS

| | | | |
|---|---|---|---|
| 1,449,165 | 3/1923 | Cameron | 128/23 |
| 3,224,437 | 12/1965 | Hardgrove | 128/23 |
| 3,743,337 | 7/1973 | Crary | 128/303 R |
| 4,044,770 | 8/1977 | Ocel et al. | 128/304 |

FOREIGN PATENT DOCUMENTS 1280339  7/1972  United Kingdom .................. 433/29

Primary Examiner—John J. Wilson
Attorney, Agent, or Firm—Jacox & Meckstroth

[57] ABSTRACT

A lighted curette which is adapted for use in removing an undesirable substance from either an ear canal or a nasal passage. The lighted curette comprises a lighting member to which is attached a handle from which extends a stem. The stem has an engagement member adjacent the end thereof for engaging and removing an undesirable substance from a nasal passage or an ear canal. Light rays are emitted from the lighting member and illuminate the engagement member. A magnification lens is attached to the lighting member for use in observing and removing the undesirable substance.

1 Claim, 8 Drawing Figures

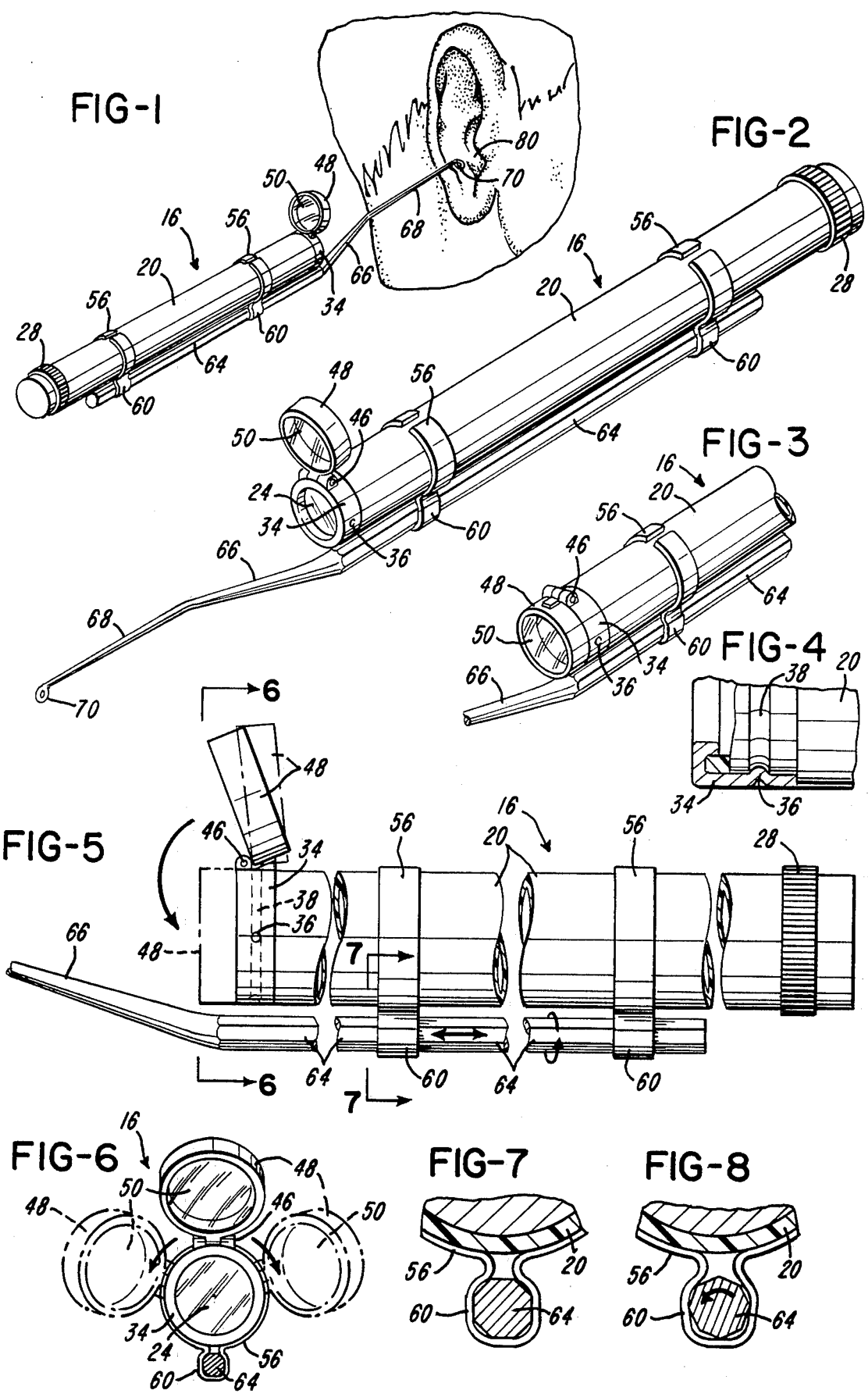

LIGHTED EAR CANAL CURETTE INSTRUMENT

BACKGROUND OF THE INVENTION

In order to remove wax or other undesirable substances from a person's ear canal, medical personnel employ a curette. Before the curette is used, a portable artificial light device, such as a flash light, is used for viewing the ear canal. Then a curette is employed to remove the wax or other undesirable substance. However, when the curette is employed the portable artificial light member is not used, due to the fact that it is difficult or impossible for a medical person to use simultaneously both a light device and a curette in cleaning an ear canal. Thus, the curette is employed in cleaning the ear canal at a time in which there is no light specifically directed into the ear canal.

It is therefore an object of this invention to provide an ear canal curette instrument which includes a lighting device, so that the ear canal is lighted while the curette is employed in cleaning the ear canal.

It is another object of this invention to provide such an instrument which includes a magnification lens device.

It is another object of this invention to provide such an instrument in which the relative positions of the curette and the lighting device are adjustable.

It is another object of this invention to provide such an instrument in which the relative positions of the curette and the magnification lens device are adjustable.

It is another object of this invention to provide a lighted curette instrument which also serves as a nasal passage curette instrument.

Other objects and advantages of this invention reside in the construction of parts, the combination thereof, the method of production and the mode of operation, as will become more apparent from the following description.

SUMMARY OF THE INVENTION

A lighted ear canal curette instrument of this invention comprises a lighting member, to which a curette member is adjustably attached. A magnification lens member is also adjustably attached to the lighting member. Thus, the ear canal is lighted and viewed through a magnification lens as the curette is employed to remove undesirable substances from the ear canal.

BRIEF DESCRIPTION OF THE VIEWS OF THE DRAWINGS

FIG. 1 is a perspective view of a lighted ear canal curette instrument of this invention, illustrating use thereof with respect to a patient's ear canal.

FIG. 2 is a perspective view of a lighted ear canal curette instrument of this invention, drawn on a larger scale than FIG. 1, and showing the instrument of this invention viewed from an angle substantially 180 degrees from that shown in FIG. 1.

FIG. 3 is a fragmentary perspective view of the instrument of this invention in the position illustrated in FIG. 2, but showing the magnification lens member in a different adjusted position.

FIG. 4 is an enlarged fragmentary sectional view showing a portion of the light emitting end of the lighting member of an instrument of this invention.

FIG. 5 is a fragmentary side elevational view, drawn on a slightly smaller scale than FIG. 4, of an instrument of this invention, illustrating the manner in which the magnification lens member and the curette are adjustable with respect to the lighting device.

FIG. 6 is a sectional view taken substantially on line 6—6 of FIG. 5.

FIG. 7 is an enlarged sectional view taken substantially on line 7—7 of FIG. 5, showing the curette in one position of rotational adjustment.

FIG. 8 is an enlarged sectional view similar to FIG. 7, but showing the curette in another position of rotational adjustment.

DETAILED DESCRIPTION OF THE INVENTION

A lighted ear canal curette instrument 16 of this invention comprises a lighting member 20, which is shown as being elongate in shape. The lighting member 20 has a lens 24 at one end thereof through which light is transmitted from a lamp, not shown, within the lighting member 20. Also within the lighting member 20 is any suitable means not shown for energization of the lamp. At the end of the lighting member 20, opposite the lens 24, is a switch operator 28 which is operably joined in a manner, not shown, to an electric switch within the lighting member 20 for energization and deenergization of the lamp within the lighting member 20.

Encompassing the lens 24 at the end of the lighting member 20 is a band 34 which has inwardly extending lobes 36 which are slidably positioned within an annular groove 38 adjacent the end of the lighting member 20. A hinge 46 attaches a housing 48 to the band 34. Within the housing 48 is a magnification lens 50.

Also encompassing the lighting member 20 are a plurality of retainer members 56. Each retainer member 56 has an extension portion 60 through which extends an elongate handle 64. Integral with the handle 64 and extending in a generally axial direction therefrom in end-to-end relationship is a stem portion 66 and a stem portion 68. The stem portion 66 is shown as being angular with respect to the handle 64, and the stem portion 68 is shown as being angular with respect to the stem portion 66. In the preferred position, the stem portion 68 is substantially coaxial with the axis of the lighting member 20. Integral with the stem portion 68 at the end thereof is an engagement member 70, which is shown as being angular with respect to the stem portion 68.

When a medical person desires to remove a substance from an ear canal 80, as illustrated in FIG. 1, the lighting member 20 is lighted by means of operation of the switch operator 28. The housing 48 of the magnification lens 50 is adjusted as desired. The housing 48 is angularly adjustable with respect to the band 34, and the band 34 is rotatable upon the housing member 20 for adjustment of the lens 50. The housing 48 is also pivotally movable to the position thereof shown in FIG. 3. This is the position of the housing 48 when the instrument is not in use.

Also, the handle 64 is rotatably adjustable with respect to the retainer members 56 for adjustment of the position of the engagement member 70. Rotational adjustment of the handle 64 adjusts the position of the engagement member 70 with respect to the lighting member 20 and with respect to the lens 50. Also, the retainer members 56 are rotatably adjustable upon the lighting member 20 to position the handle at any desired rotative position with respect to the lighting member 20.

Thus, it is understood that a medical person can easily, readily, and carefully remove a substance from the ear canal 80.

The lighted curette instrument of this invention is also used to remove undesirable substances from a nasal passage.

Although the preferred embodiment of the lighted ear canal curette instrument of this invention has been described, it will be understood that within the purview of this invention various changes may be made in the form, details, proportion and arrangement of parts, the combination thereof, and the mode of use, which generally stated consist in an instrument within the scope of the appended claims.

The invention having thus been described, the following is claimed:

1. A lighted ear canal/nasal passage cleaning instrument of the type provided with an elongate lighting member having a central axis and having a light emitting end portion from which light is emitted, the instrument also being of the type in which a magnification lens is attached to the elongate lighting member adjacent the light emitting end portion, the magnification lens extending laterally from the elongate lighting member and being angularly adjustable with respect to the elongate lighting member, the improvement comprising:

an elongate handle attached to the elongate lighting member and extending along the length thereof, the elongate handle being parallel to the elongate lighting member and in juxtaposition therewith, the handle having an end portion, a stem integrally attached to the end portion of the handle and extending angularly from the end portion of the handle, the stem also extending angularly from the lighting member, the stem having an end portion, a curette type engagement member integrally attached to the end portion of the stem, the curette type engagement portion extending angularly from the stem and positioned in alignment with the central axis of the lighting member.

* * * * *